United States Patent [19]

Kyle

[11] 4,456,786

[45] Jun. 26, 1984

[54] TERMINAL ASSEMBLY FOR HEART PACEMAKER

[75] Inventor: James C. Kyle, 24372 Via San Clemente, Mission Viejo, Calif. 92675

[73] Assignee: James C. Kyle, Roseburg, Oreg.

[21] Appl. No.: 322,013

[22] Filed: Nov. 16, 1981

Related U.S. Application Data

[63] Continuation of Ser. No. 95,613, Nov. 19, 1979, abandoned.

[51] Int. Cl.³ .................... H01B 17/26; C03C 27/02
[52] U.S. Cl. .................... 174/152 GM; 65/21.1; 65/33; 65/59.34; 65/59.35; 128/419 P; 428/426
[58] Field of Search ........... 174/50.58, 50.61, 151, 174/152 GM; 65/59.1, 59.3, 59.31, 59.34, 59.35, 59.4, 59.5, 59.6; 128/419 P; 403/28, 29, 30, 179

[56] References Cited

U.S. PATENT DOCUMENTS

| | | | |
|---|---|---|---|
| 2,138,660 | 11/1938 | Mann | 174/152 GM X |
| 2,174,375 | 9/1939 | Beggs | 174/152 GM X |
| 2,188,061 | 1/1940 | Scharfnagel | 174/50.61 X |
| 3,225,132 | 12/1965 | Baas et al. | 174/151 |
| 3,258,350 | 6/1966 | Martin et al. | 174/50.61 X |
| 3,540,895 | 11/1970 | Scheidler et al. | 65/33 X |
| 3,920,888 | 11/1975 | Barr | 174/152 GM |
| 4,010,759 | 3/1977 | Boer | 174/152 GM X |

FOREIGN PATENT DOCUMENTS

| | | | |
|---|---|---|---|
| 749540 | 12/1966 | Canada | 174/152 GM |
| 948626 | 9/1956 | Fed. Rep. of Germany | 174/152 GM |

*Primary Examiner*—Laramie E. Askin
*Attorney, Agent, or Firm*—Ellsworth R. Roston; Charles H. Schwartz

[57] ABSTRACT

First and second members spaced from each other are hermetically sealed by fused insulating materials. The insulating materials are partially amorphous and partially crystalline. The insulating materials have substantially identical characteristics. However, a first one of the insulating materials is more crystalline than a second one of the insulating materials.

A third insulating material may also be included and may be more crystalline than the first insulating material. The first, second and third crystalline materials may have substantially identical compositions.

The second insulating material may have nonwetting characteristics relative to the second member. This causes the second insulating member to have a domed configuration to increase the length of the dielectric leakage path. The third insulating material may be spaced from the second insulating material and may be provided with a flat surface to receive other members in abutting relationship.

The first and second members and the insulating materials may be disposed on a lid in a heart pacemaker. The first member may be a terminal pin made from a noble metal and the second member may be a ferrule made from titanium or a titanium alloy.

The heart pacemaker may also have third and fourth members respectively corresponding to the first and second members and may further have insulating materials between the third and fourth members as described above. Additional insulating material may envelop the second and fourth members.

32 Claims, 5 Drawing Figures

TERMINAL ASSEMBLY FOR HEART PACEMAKER

This is a continuation of application Ser. No. 095,613, filed Nov. 19, 1979, now abandoned.

This invention relates to a terminal for maintaining an electrical terminal pin in insulated relationship to a lid on a housing. More particularly, the invention relates to a terminal for maintaining the electrical terminal pin in insulated relationship to a lid with a long dielectric leakage path between the terminal pin and the lid. The invention further relates to a method of forming such a terminal. The invention has particular applicability to a terminal for a heart pacemaker.

In recent years, considerable advances have been made in medical technology involving the treatments of patients with heart problems. For example, patients having defective hearts have received heart pacemakers which produce signals at a particular frequency and stimulate the heart so that the heart pumps blood through the patient at that frequency. Initially, the heart pacemakers were disposed externally. However, with recent advances in the construction of the heart pacemakers and in medical technology, the heart pacemakers are often disposed within the body of the patient.

In spite of the considerable advances which have been made, some problems still exist in heart pacemakers. For example, it is important that the heart pacemaker be installed in a patient's body easily and efficiently. If the heart pacemaker is not installed easily and efficiently, the patient suffers inconveniences. Sometimes these inconveniences become sufficiently serious so that the health of the patient is endangered or even impaired.

A terminal for a heart pacemaker is disclosed in copending application Ser. No. 870,192 filed by James C. Kyle et al on Jan. 17, 1978, (now U.S. Pat. No. 4,220,814) and assigned of record to the assignee of record of this application. This terminal solves many of the problems previously experienced in terminals for heart pacemakers. However, difficulties are occasionally experienced with this terminal in assembling the terminal in the heart pacemaker and in installing the pacemaker in the body of a patient. For example, difficulty has been occasionally experienced in the fracture of an insulating sleeve defining the outer boundary of the terminal when the terminal has been assembled in the pacemaker or the pacemaker has been installed in a patient's body. The fracture of this insulating sleeve has sometimes impaired the characteristics of the terminal in providing an electrical insulation.

This invention provides a terminal which overcomes the above disadvantages. The terminal is assembled in such a manner that no parts in the terminal can be impaired during assembly in a pacemaker or during installation of the pacemaker in a patient's body. As a result, the patient suffers minimal inconvenience without any possibility that the pacemaker will have to be removed shortly after installation and a new pacemaker installed.

In one embodiment of the invention, first and second members spaced from each other are hermetically sealed by fused insulating materials. The insulating materials are partially amorphous and partially crystalline. The insulating materials have substantially identical characteristics. However, a first one of the insulating materials is more crystalline and more viscous than a second one of the insulating materials. The first insulating material may also have a higher melting temperature than the second insulating material.

A third insulating material may also be included and may be more crystalline and more viscous than the first insulating material. The third insulating material may also have a higher melting temperature than the first insulating material. The first, second and third crystalline materials may have substantially identical compositions.

The first and second members and the insulating materials may be disposed on a lid in a heart pacemaker. The first member may be a terminal pin made from a noble metal and the second member may be a ferrule made from titanium or a titanium alloy. The ferrule may be disposed in enveloping relationship to the terminal pin and the insulating material may be disposed between the terminal pin and the ferrule in hermetically sealed relationship to these members.

The second insulating material may have nonwetting characteristics relative to the second member. This causes the second insulating member to have a domed configuration, which produces an increase in the length of the dielectric leakage path. The third insulating material may be spaced from the second insulating material and may be provided with a flat surface to receive other members in abutting relationship. For example, when the combinations of elements described above are used in a heart pacemaker, a filter may be disposed against the flat surface of the third insulating material to provide a firm and predictable relationship between the insulating material and the filter.

The heart pacemaker may also have third and fourth members respectively corresponding to the first and second members and may further have insulating materials between the third and fourth members as described above. Additional insulating material may envelop the second and fourth members.

The ferrule may be provided with a threaded external configuration. This threaded configuration facilitates the threaded assembly of the ferrule into a block supporting an electrical lead. This electrical lead is coupled electrically to the heart pacemaker of the patient. Because of the threaded relationship between the ferrule and the block, the terminal may be assembled into the heart pacemaker easily and efficiently by the manufacturer of the heart pacemaker.

When first and second insulating materials or first, second and third insulating materials are used as described above, the combinations of insulating materials may have considerably wider applications than in terminals for heart pacemakers. However, such combinations of insulating materials are particularly adapted for use in terminals for heart pacemakers.

Figure 1:
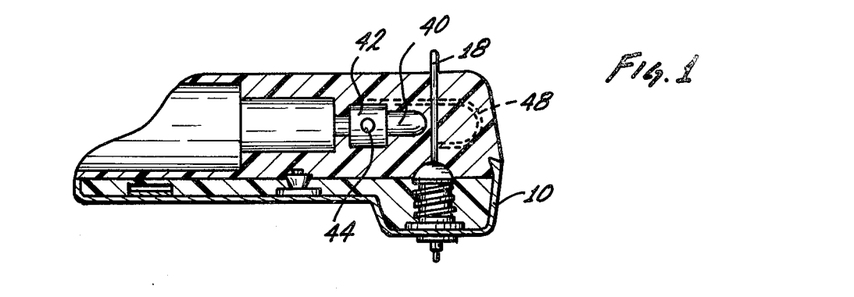
FIG. 1 is an elevational view, at least partially in section of a terminal for a heart pacemaker.

In one embodiment of the invention, a lid 10 is provided with an aperture 12. A ferrule 14 preferably having a hollow cylindrical configuration is disposed within the aperture 12 and is provided with a flange 16 which rests on the lid 10. The flange 16 of the ferrule 14 is welded as at 17 to the lid 10 around the periphery of the flange. The ferrule 14 may be made from a suitable material such as titanium or a titanium alloy. For example, the titanium alloy may be obtained from Titanium Metals Corp. One such an alloy is designated as an alloy (Ti6Al14V), and provides 6 percent aluminum, 4 percent vanadium, and 90% titanium. Said alloy provides a higher mechanical strength than pure titanium.

An electrical terminal pin 18 preferably made from a suitable material such as a noble metal is disposed within the ferrule 14 in concentric relationship to the ferrule. Preferably, the terminal pin 18 is made from platinum. The terminal pin 18 is hermetically sealed to the ferrule 14 by insulating material generally indicated at 20. Insulating material suitable for use as the material 20 is fully disclosed in copending application Ser. No. 840,740 filed by James C. Kyle on Oct. 11, 1977, now abandoned in favor of continuation application Ser. No. 229,151, filed Jan. 28, 1981, (now U.S. Pat. No. 4,421,947) both assigned of record to the assignee of record of this application. Such a material is particularly advantageous because it provides a high electrical impedance and maintains a hermetic seal between the terminal pin 18 and the ferrule 14 even when the pin is subjected to considerable bending and twisting forces. The material is also advantageous because it has a coefficient of thermal expansion substantially corresponding to that of the ferrule 14, thereby maintaining the hermetically sealed relationship with changes in temperature.

The insulating material 20 may include a first portion 22, a second portion 24 and a third portion 26. The portion 24 is fused to the portion 22 at the end of the portion 22 displaced from the lid 10 and the portion 26 is fused to the portion 22 at a position relatively near the lid. All of the portions 22, 24 and 26 have a partially amorphous and partially crystalline composition. However, the portion 22 is more crystalline and more viscous than the portion 24 and is less crystalline and less viscous than the portion 26. Furthermore, the portion 22 preferably has a higher melting temperature than the portion 24 and a lower melting temperature than the portion 26.

The portions 22, 24 and 26 preferably have substantially the same composition with relatively minor differences. This causes the portions 22, 24 and 26 to be compatible in such parameters as coefficient of thermal expansion, electrical resistance and response to thermal and mechanical shock. However, the increase in the amorphous properties of the portion 24 relative to the portion 22 causes the portion 24 to have nonwetting characteristics relative to the ferrule 14. Because of these nonwetting characteristics, the portion 24 assumes essentially a hemispherical shape to minimize contact with the ferrule 14. This essentially hemispherical shape increases the length of the dielectric path between the terminal pin 18 and ferrule 14 and accordingly increases the electrical resistance between the terminal pin and ferrule.

Figure 2:
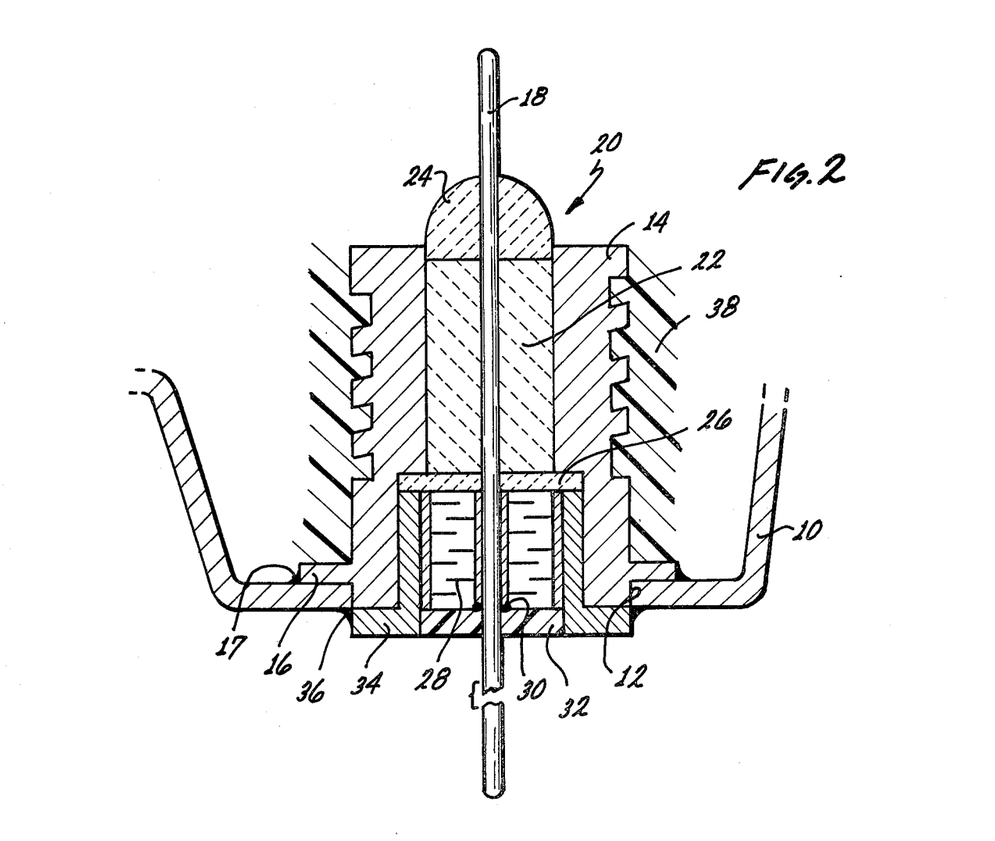
FIG. 2 is an enlarged fragmentary sectional view in elevation of a portion of the terminal shown in FIG. 1.

The increase in crystallinity of the portion 26 relative to the portion 22 causes the bottom surface of the portion 26 to have essentially a flat configuration. Because of this flat configuration, an electrical filter 28 can be disposed on the terminal pin 18 within the hollow configuration of the ferrule 14 in abutting relationship to the portion 26 along the complete area of the flat surface. The filter 28 has characteristics for passing signals only in a particular range of frequencies such as approximately low pass range of approximately 10 megahertz. For example, the filter 28 may have 6 db attenuation characteristics at approximately 10 megahertz, 40 db attenuation characteristics at approximately 100 megahertz and 60 db attenuation characteristics at approximately 1 gigahertz, thereby affecting rejection of unwanted interfering R.F. signals. As shown in FIG. 2, the filter 28 may be disposed at least partially within the heart pacemaker. The filter 28 may be constructed in a conventional manner from a plurality of spaced plates or discs to define a capacitive filter. The filter 28 may be attached to the terminal pin 18 by solder as at 30.

The filter 28 may be maintained in fixed relationship within the ferrule 14 by a spacer 34 made from a suitable material such as nickel or a nickel-iron-cobalt alloy designated by the trademark "Kovar" when the ferrule is made of titanium. The spacer 34 is provided with a hollow cylindrical body and with a flange which is disposed against the bottom of the ferrule 14. The spacer 34 is attached to the ferrule 14 at 36 as by projection welding. Projection welding is desirable since it provides localized heating without affecting the solder attachment 30.

The ferrule 14 is preferably provided with a threaded configuration at its external surface. This facilitates the bond between the ferrule and a suitable filler 38 such as a thermal-setting epoxy which is disposed around the ferrule. The epoxy may be purchased commercially. For example, a commercially granulated epoxy may be purchased from Hysol in Pasadena, Calif., for use as the filler 38.

A suitable adhesive such as a thermal-setting epoxy is disposed as a filler 32 on the bottom side of the filter 28 to maintain the filter in fixed position relative to the ferrule. The epoxy may be purchased from Hysol and may have the same composition as the filler 38.

A catheter block (or electrical body) 40 is connected electrically to the terminal pin 18 at the end of the terminal pin opposite from the lid 10. The block 40 may be made from a suitable material such as titanium or a suitable alloy such as that designated as "Elgiloy" alloy by Elgin Watch Company or such as that designated as "Haynes 25" by the Haynes Stellite Company. The electrical body 40 is provided with an extension 42 and an aperture 44 is provided in the extension so that an electrical connection 48 from the terminal pin 18 can be connected electrically to the electrical body. The terminal pin 18 may be connected electrically to the electrical body as by welding.

The portion 22 of the insulating material 20 may be made in the manner disclosed and claimed in application Ser. No. 840,740 filed by James C. Kyle on Oct. 11, 1977, now abandoned in favor of continuation application Ser. No. 229,151, filed Jan. 28, 1981, (now U.S. Pat. No. 4,421,947) both assigned of record to the assignee of record of this application. For example, the portion 22 may include a pair of fluxes having different melting temperatures. Preferably, one of the fluxes has a melting temperature greater by several hundred degrees Fahrenheit, such as approximately 200° F. to 300° F., than the other flux. By way of illustration, one of the fluxes (flux A) may have a melting temperature of approximately 800° F. and a composition as follows:

| Material | Relative Percentage by Weight |
|---|---|
| Lead oxide (PbO) | 68.5 |
| Boric oxide ($B_2O_3$) | 10.5 |
| Silicon dioxide ($SiO_2$) | 21.0 |

The other flux (flux B) may have a melting temperature of approximately 1000° F. and a composition as follows:

| Material | Relative Percentage by Weight |
|---|---|
| Lead oxide (PbO) | 80.0 |
| Boric oxide ($B_2O_3$) | 20.0 |

Fluxes A and B tend to constitute eutectics which effectively lower the melting point of the boric oxide in the fluxes.

When fluxes A and B are provided as specified above, flux A may have a relative percentage by weight in the material of approximately fifteen percent (15%) to twenty-five percent (25%) and flux B may have a relative percentage by weight in the material of approximately forty percent (40%) to fifty-five percent (55%). A stuffing material having properties of becoming crystalline is also provided in the material in a percentage by weight of approximately twenty percent (20%) to forty-five percent (45%).

The crystal stuffing includes oxides of zinc and zirconium and silicon dioxide to provide for the formation of crystals in at least a portion of the material. The oxides of zinc and zirconium and the silicon dioxide may be included in such forms as zinc zirconium silicate, zirconium spinel and zirconium silicate. For example, the crystal stuffing may be formed from the following materials in the following percentages by weight:

| Material | Relative Percentage by Weight |
|---|---|
| Lead antimonate ($Pb_3(SbO_4)_2)_2$ composed of lead, antimony and oxygen | 2 |
| Zinc zirconium silicate | 31 |
| Zirconium spinel | 33 |
| Zirconium silicate | 34 |

The crystal stuffing specified above has particular utility in hermetically sealing pure titanium.

To form the portion 22 of the insulating material 20 and to produce hermetic seals with such material, fluxes A and B are first smelted separately and quenched in water to frit the material. For example, flux A may be smelted for a period of approximately two (2) hours at a temperature of approximately 1500° F. and then quenched in water, and flux B may be smelted for a period of approximately one (1) hour at a temperature of approximately 1200° F. and then quenched in water. The crystal stuffing is smelted for a period of approximately three (3) hours at a temperature of approximately 1800° F. and is then quenched in water.

The fritted fluxes and the crystal stuffing are then mixed in the desired percentages and ground such as in a ball mill for a period of approximately three (3) to four (4) hours. The resultant material is then heated to a temperature of approximately 1200° F. to 1300° F. for a period of approximately two (2) to three (3) hours. Preferably the material is stirred periodically such as every fifteen (15) minutes while it is being heated. The temperatures and times chosen for such heating operation are such as to partially combine the different compounds in the mixture. As a result, the material is predominantly amorphous but a portion has become crystalline. For example, approximately eighty percent (80%) of the material may be amorphous and approximately twenty percent (20%) may be crystalline. The material is then converted to a frit by quenching in water. The resultant material has a melting temperature of approximately 1100° F.

The material is then heated to a temperature slightly above its melting temperature for a period of time dependent upon the characteristics desired for the material. For example, the material may be heated to a temperature of approximately 1200° F. (100° F. above the melting temperature) for a period of approximately three (3) to four (4) hours. The material slowly changes from an amorphous glass to a ceramic as it is being heated. Furthermore, the coefficient of thermal expansion of the material slowly decreases as the material becomes progressively crystalline.

The temperature and duration of the heating operation are chosen so that the coefficient of thermal expansion of the material is slightly greater than the coefficient of thermal expansion of the member, such as the ferrule 14, to be sealed. The temperature and duration of the heating operation are such that the material is approximately fifty percent (50%) amorphous and approximately fifty percent (50%) crystalline or slightly more crystalline than amorphous.

The fritted material is then pulverized and separated into different sizes. Beads are then formed by mixing particles of different sizes with a suitable material such as polyethylene glycol (marketed under the name "Carbowax") or an animal fat and pressing the particles together. For example, approximately forty percent (40%) of particles by weight of 150 mesh, approximately fifty percent (50%) of particles of 300 mesh and approximately ten percent (10%) of particles above 300 mesh may be mixed with polyethylene glycol or an animal fat where the polyethylene glycol or the animal fat comprises one and one-half percent (1.5%) to three percent (3%) by weight in the mixture. The particles may then be pressed together to form the beads.

The beads are then disposed between the terminal pin 18 and the ferrule 14. The combination is then heated to a suitable temperature such as approximately 1225° F. for a suitable period of time such as a period to approximately thirty (30) minutes. The material then becomes fused to the terminal pin 18 and the ferrule 14. Since the combination is heated for only a relatively short period of time, the crystal structure of the portion 22 of the insulating material 20 is not changed significantly during the heating operation.

The fusion of the portion 22 of the material 20 to the ferrule 14 is facilitated by cooling the material rapidly in air. This causes the portion 22 of the material 20 to press against the ferrule 14 as it is rapidly cooled, particularly since the coefficient of thermal expansion of the material 20 is slightly greater than that of the ferrule 14. By pressing against the ferrule during such cooling, the material facilitates the production of a hermetic seal with the ferrule.

The hermetic seal between the material 20 and the ferrule 14 is produced in various ways. For example, a thin polycrystalline layer is produced in the material at the boundary with the ferrule 14. For example, zinc silicate ($Zn_2SiO_4$) or a relatively complex compound of zinc, oxygen and silicon ($2ZnO.SiO_2$) having the same chemical composition as zinc silicate or a combination of both is formed at such boundary. These crystals tend to become formed in the presence of lead or antimony. These zinc compounds become crystallized in the form of Willemite crystals. Furthermore, crystals of zirconium silicate also become produced at such boundary.

The crystallization of the zirconium silicate occurs in the presence of lead. The crystallization of the zirconium silicate is facilitated by the inclusion of zinc zirconium silicate in the mixture since this compound tends to become dissolved at a lower temperature than zirconium silicate. Zinc zirconium silicate and zirconium silicate tend to exist as natural minerals and are preferably used in this form.

The Willemite crystals are of a different size and shape than the crystals of zirconium silicate. For example, the crystals of zirconium silicate tend to be smaller than the Willemite crystals. This causes nucleations of different sizes to be produced and facilitates the flexing and bending of the crystalline layer adjacent the ferrule when subjected to thermal and mechanical shocks. In this way, the hermetic seal is maintained even when the material is subjected to severe thermal or mechanical shocks.

Zirconium spinel tends to increase the mechanical strength of the material. When introduced into the material, zirconium spinel is already in crystalline form so that it does not change as the material is heated and cooled as specified above. As a result, zirconium spinel acts as a filler in the material. Zirconium spinel tends to exist as a natural mineral and is preferably used in this form.

An oxygen valence bond is also produced between the material and the ferrule to facilite the formation of a hermetic seal between them. This oxygen valence bond results from a chemical bond between oxygen atoms in the material and atoms on the surface of the ferrule 14. In other words, the oxygen is shared by the layer on the surface of the ferrule 14 and the material constituting this invention. This oxygen valence bond is produced during the heating of the material and the ferrule to the relatively high temperatures.

When an alloy of titanium is used as the ferrule 14, the alloy often has a composition of Ti6A14V. In other words, one (1) molecule of titanium is combined with six (6) molecules of aluminum and four (4) molecules of vanadium. Such an alloy is advantageous because the surface of the alloys tends to form oxides of titanium, vanadium and aluminum and these oxides tend to become bound to the portion 22 of the insulating material 20 by oxygen valence bonding. Thus, the inclusion of the other metals with titanium in the alloy tends to facilitate the hermetic seal with the portion 22 of the insulating material 20.

Because of the random orientation of the polycrystalline structure and the oxygen valence bonding of the oxygen to the external surface of the ferrule 14, the material does not fragment or crumble in use, even when subjected to thermal and mechanical shocks. For example, any tendency for the material to crack occurs radially toward the terminal pin 18 so as to preserve the characteristics of the material in providing an electrical insulation.

The portion 22 of the material 20 is also hermetically sealed to the terminal pin 18. For example, when the terminal pin 18 is made from platinum, the platinum tends to become chemically etched at its surface to a minor extent. This etching occurs from the action on the platinum, during the smelting and fusing operations, of the material constituting this invention. This etching may penetrate the surface of the platinum to a thickness of approximately one half mil (0.0005") to one mil (0.001") when the terminal pin has a thickness of approximately thirty mils (0.030"). The material constituting this invention then tends to become locked in the irregular surface produced in the surface of the terminal pin 18 as a result of such penetration.

The bond between the platinum terminal pin and the portion 22 of the insulating material 20 is actually quite thin in physical dimensions. This bond has a thickness in the order of twenty Angstroms (20 A). The material of this invention at the surface of the platinum terminal pin tends to be more amorphous than the material at the surface of the ferrule 14, particularly when the ferrule is made from titanium or a titanium alloy.

At distances removed from the ferrule 14, the portion 22 of the material 20 is more amorphous than at the boundary with the ferrule 14. Thus, the portion 22 of the material 20 may be almost entirely crystalline at the boundary with the ferrule 14. However, at positions somewhat removed from the ferrule 14, the portion 22 of the material 20 may be predominantly amorphous.

The combination of amorphous and crystalline properties for the material 20 provides certain advantages in addition to those discussed above. For example, the crystalline structure in the material 20 normally has an alpha ($\alpha$) phase at relatively low temperatures but the characteristics of the crystalline structure change from the alpha ($\alpha$) phase to the beta ($\beta$) phase as the temperature of the material increases from approximately 800° F. to approximately 1400° F. For example, the coefficient of thermal expansion of the crystalline structure in the beta ($\beta$) phase is different from that in the alpha ($\alpha$) phase.

The partially amorphous characteristics of the portion 22 of the material 20 tend to compensate for effects resulting from a transition in the crystalline structure between the alpha ($\alpha$) phase and the beta ($\beta$) phase. The interleaved characteristics of the polycrystalline structure at the boundary with the ferrule 14 also tend to compensate for any changes in the crystalline structure of the material 20 between the alpha ($\alpha$) phase and the beta ($\beta$) phase.

The titanium alloy also has alpha ($\alpha$) and beta ($\beta$) phases. However, these phases are stabilized so that each phase exists over a relatively wide range of temperatures. These different phases are partially instrumental in causing the titanium alloy to be stronger than pure titanium. This is particularly true when the titanium alloy is heat treated.

The phase of the titanium alloy changes from alpha ($\alpha$) to beta ($\beta$) at a temperature of approximately 1300° F. However, a relatively long period of time at a temperature of approximately 1300° F. is required for the titanium alloy to change from the alpha ($\alpha$) phase to the beta ($\beta$) phase. The coefficient of thermal expansion of the titanium alloy in the alpha ($\alpha$) phase is different from that in the beta ($\beta$) phase.

The polycrystalline structure of the material facilitates the retention of a hermetic seal as the titanium alloy changes from the alpha ($\alpha$) phase to the beta ($\beta$) phase. This results from the ability of the polycrystalline layer to adapt to differences in the expansion characteristics of the titanium alloy with changes in temperature. The oxygen valence bond between the ferrule 14 and the portion 22 of the material 20 also facilitates the maintenance of the hermetic seal under such circumstances.

The portion 22 of the material 20 is highly resistant to strong acids and alkalis. As will be appreciated, this is important when the material is used in a heart pacemaker since the heart pacemaker is generally disposed in the body of a patient and is accordingly subjected to the fluids in the body of the patient.

The portion 22 of the material 20 also provides other advantages of some importance. For example, the material provides a high dielectric constant considerably greater than that of most other materials now in use. By way of illustration, the electrical insulation between the terminal pin 18 and the ferrule 14 is as high as $10^{18}$ ohms. This is important in such equipment as heart pacemakers which have to operate satisfactorily under all of the adverse sets of circumstances which a human body is capable of producing.

The portion 22 of the material 20 also has other advantages of some importance. For example, when the operation of hermetically sealing the terminal pin 12 and the ferrule 14 has been completed, tests are made to determine if a hermetic seal has actually been produced. If a hermetic seal has not been produced, the combination of the terminal pin, the ferrule and the material may be fused at the temperature of approximately 1225° F. for an additional period to approximately thirty (30) minutes. Since the material is still somewhat amorphous, this additional fusing operation tends to facilitate the creation of the oxygen valence bond between the material and the ferrule. It also tends to facilitate the creation of a polycrystalline structure in the material, particularly at the surface adjacent the ferrule. As a result, any failure to produce a hermetic seal tends to become corrected.

The portion 24 of the insulating material 20 may be provided with a composition quite close to that described above for the portion 22. However, more of flux A is included in the mixture than described above. For example, an increase in flux A in the range of approximately four percent (4%) to ten percent (10%) by weight may be provided in the mixture. This causes the portion 24 to have a lower melting temperature and to be less viscous than the portion 22. It also causes the portion 24 to be more amorphous than the portion 22.

The portion 26 may actually be formed from materials having the relative proportions described above for the portion 22. However, the portion 26 may include a relatively inert filler such as a colloidal clay designated as bentonite. The inclusion of bentonite tends to increase the melting temperature of the portion 26 relative to that of the portion 22 and tends to make the portion 26 more viscous and more crystalline than the portion 22. By way of illustration, bentonite may be included in the portion 26 in a proportion to twenty percent (20%) by weight. This increased crystallinity of the portion 26 causes the portion to function as a barrier in preventing undesirable materials from pervading the insulating material 20. It also serves as a mechanical barrier in absorbing mechanical shocks.

The portions 22, 24 and 26 may be individually mixed, melted and fritted substantially in the manner described above. The fritted material for the portions 22, 24 and 26 may then be formed as beads substantially as described above. The beads may then be disposed between the terminal pin 18 and the ferrule 14 in the relative spacing shown in FIG. 1 and described above for the portions 22, 24 and 26. The assembled terminal may then be heated to a suitable temperature such as approximately 1225° F. for a suitable period of time such as a period to approximately thirty (30) minutes to fuse the portions 22, 24 and 26 to one another and to the terminal pin 18 and the ferrule 14. The terminal may be subsequently cooled rapidly in air to facilitate the production of a hermetic seal between the terminal pin 18 and the ferrule 14.

Figure 3:
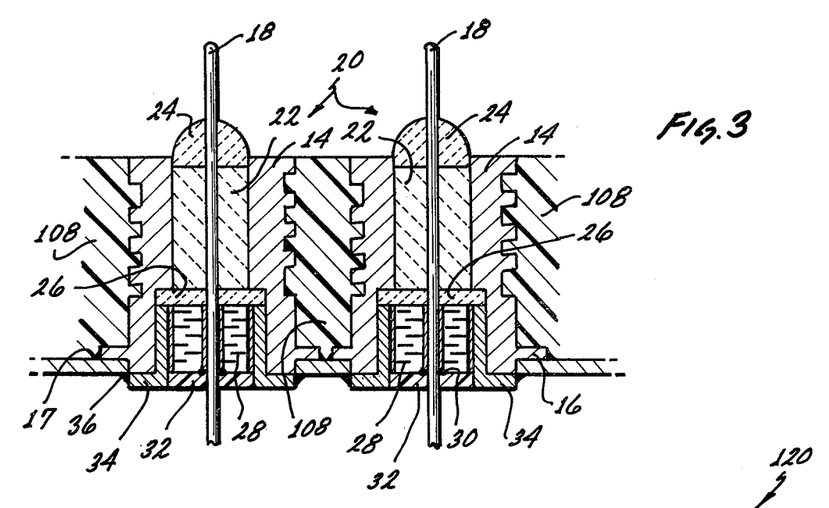
FIG. 3 is an enlarged fragmentary sectional view; similar to that shown in FIG. 2, of a terminal constituting a second embodiment of the invention.

FIG. 3 illustrates an arrangement for insulating each of two separate leads 100 and 102 in the manner described above. The lead 100 may introduce the signals to the heart of the patient. The lead 102 may be introduced to an electrical coupling 104 (FIG. 4) which is disposed in the body of a patient to serve as a ground. Such an arrangement is desirable because it provides a minimum jolt to a patient when the heart pacemaker is triggered into introducing signals to the heart of the patient. Each of the leads 100 and 102 may be insulated relative to an associated ferrule by insulating material corresponding to the portions 22, 24 and 26 described above. A suitable filler 108 such as an epoxy may be provided in enveloping relationship to the ferrules 14.

Figures 4, 5:
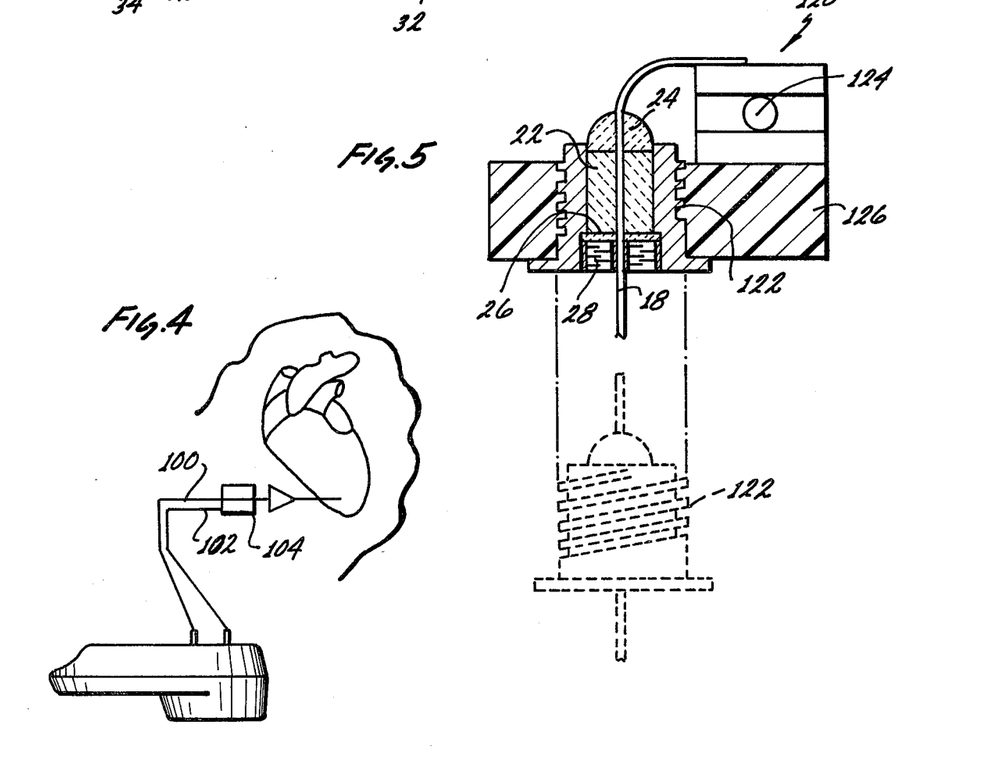
FIG. 4 is a view schematically showing the coupling to the heart of a patient of the terminal shown in FIG. 3.
FIG. 5 is a view schematically showing in solid lines the installation of the terminal of FIGS. 1 and 2 into an electrical block providing a lead for connection to the heart and schematically showing in broken lines the terminal before installation into the electrical block.

The terminals described above may be easily coupled to a block generally indicated at 120 in FIG. 5. This results from the threaded configuration at the external surface of the ferrule 14. Because of this threaded configuration, the terminal may be screwed into a threaded socket 122 in an insulated portion 126 of the block. An electrical connection may then be made from the terminal pin such as the terminal pin 18 to the wall of the block 120 to provide electrical continuity between the terminal pin and a lead 124 extending from the block to the heart of the patient.

The term "terminal pin" in the claims is intended to mean any type of electrically conductive member. The term "ferrule" is intended to mean any type of electrically conductive member spaced from the terminal pin.

Although this application has been disclosed and illustrated with reference to particular applications, the principles involved are susceptible of numerous other applications which will be apparent to persons skilled in the art. The invention is, therefore, to be limited only as indicated by the scope of the appended claims.

I claim:

1. In combination in a terminal assembly for a heart pacemaker,
   a lid for the heart pacemaker,
   a hollow ferrule attached to the lid,
   a terminal pin extending through the ferrule in spaced relationship to the ferrule,
   a first insulating material disposed between the ferrule and the terminal pin and sealing the ferrule and the terminal pin, and
   a dome of a second insulating material disposed on the first insulating material in fused relationship with the first insulating material, the second insulating material being formed from the same chemicals as the first insulating material but in slightly different percentages than the first insulating material,
   the second insulating material having non-wetting characteristics relative to the ferrule to provide for the formation of the dome.

2. The combination set forth in claim 1, including, a third insulating material formed from the same chemicals as the first and second insulating materials but in slightly different percentages than each of the first and second insulating materials, the third insulating material being disposed against the first insulating material on the opposite side of the first insulating material from the second insulating material, the third insulating material having a flat surface on the side opposite the side common with the first insulating material.

3. The combination set forth in claim 1 wherein the first and second insulating materials are partially amorphous and partially polycrystalline and the second insulating material is more amorphous than the first insulating material.

4. The combination set forth in claim 3, including, a third insulating material which is partially amorphous and partially crystalline and which is disposed against the first insulating material on the opposite side of the first insulating material from the second insulating material, the third insulating material being formed from the same chemicals as the first and second insulating materials in such proportions as to make the third insulating material more crystalline than the second insulating material.

5. The combination set forth in claim 4 wherein the first, second and third insulating materials are fused and wherein the chemicals in the first and third insulating materials have individual proportions to make the third insulating material more crystalline than the first insulating material.

6. The combination set forth in claim 5 wherein each of the first, second and third insulating materials includes the oxides of lead, silicon, boron, zinc and zirconium in percentages to provide the first insulating material with a higher melting temperature than the second insulating material and a lower melting temperature than the third insulating material.

7. The combination set forth in claim 3 wherein the first insulating material includes the oxides of lead, silicon, boron, zinc and zirconium and the second insulating material includes the oxides of lead, silicon, boron, zinc and zirconium in percentages relative to the percentages in the first insulating material to provide the second insulating material with a lower melting temperature than the first insulating material.

8. The combination set forth in claim 1 wherein the ferrule is provided with a threaded configuration at its exterior periphery and wherein a filler having insulating properties is disposed around the ferrule and in the threads to maintain the ferrule in fixed position.

9. In combination in a terminal assembly for a heart pacemaker,
a lid,
a terminal pin extending through the lid,
a hollow ferrule enveloping the terminal pin in spaced relationship to the terminal pin,
a first insulating member disposed between the terminal pin and the ferrule in hermetically sealed and directly fused relationship to the terminal pin and ferrule and having partially crystalline and partially amorphous characteristics, and
a second insulating member disposed upon the first insulating member in directly fused relationship to the first insulating member and hermetically sealed to the terminal pin and the hollow ferrule and in enveloping relationship to the terminal pin, the second insulating member being partially crystalline and partially amorphous but being more amorphous than the first insulating member.

10. The combination set forth in claim 9 wherein the second insulating member has non-wetting characteristics relative to the ferrule and has a substantially hemispherical configuration in its external periphery to increase the path of electrical leakage.

11. The combination set forth in claim 10 wherein the terminal pin is made from a noble metal and the ferrule is made from a material selected from the group consisting of titanium and a titanium alloy.

12. The combination set forth in claim 9, including, a third insulating member disposed upon the first insulating member in fused relationship to the first insulating member and in enveloping relationship to the terminal pin, the third insulating member being on the opposite side of the first insulating member from the second insulating member, the third insulating member being partially crystalline and partially amorphous but being more crystalline than the second insulating member.

13. The combination set forth in claim 12 wherein the first, second and third insulating members have compositions of the oxides of lead, silicon, boron, zinc and zirconium and the oxides of lead, silicon and boron are included in a flux having a range of approximately fifteen percent (15%) to twenty-five percent (25%) by weight in the first, second and third insulating members.

14. The combination set forth in claim 13 wherein each of the first, second and third members cumulatively includes the oxides of zinc and zirconium and the oxides of zinc and zirconium are included in stuffing materials having a range of approximately twenty percent (20%) to forty-five percent (45%) by weight in each of the first, second and third members.

15. The combination set forth in claim 14 wherein the terminal pin is made from a noble metal and the ferrule is made from a material selected from the group consisting of titanium and a titanium alloy.

16. The combination set forth in claim 12 wherein the ferrule is externally threaded and a filler having insulating properties is disposed externally of the ferrule and in the threads to maintain the ferrule in fixed position.

17. The combination set forth in claim 9 wherein the first and second insulating members have compositions of the oxides of lead, silicon, boron, zinc and zirconium and wherein the first insulating member has compositions of the oxides of lead, silicon, boron, zinc and zirconium in slightly different proportions than the second insulating member and the oxides of zinc and zirconium are included in a stuffing material having a range of approximately twenty percent (20%) to forty-five percent (45%) by weight in the first and second insulating members.

18. In combination in a terminal assembly,
a first member,
a second member disposed in spaced relationship to the first member,
a first insulating material formed from particular chemicals and disposed between the first and second members in hermetically sealed relationship to the first and second members and having a partially crystalline and partially amorphous composition and having a greater concentration of crystals at the boundary with the second member than at positions removed from such boundary, and a second insulating material formed from the particular chemicals in a different proportion than the proportion of the particular chemicals in the first insulating material, the second insulating material being fused with the first insulating material and hermetically sealed to the first and second members, the second insulating material being partially crystalline and partially amorphous and being more amorphous than the first insulating material.

19. The combination set forth in claim 18, including, the second insulating material being less viscous than the first insulating material and having non-wettable properties relative to the second member and being disposed in the shape of a dome on the first insulating material to increase the path of electrical leakage.

20. The combination set forth in claim 19 wherein the first member is made from a noble metal and the second member is made from a material selected from the group consisting of titanium and a titanium alloy.

21. The combination set forth in claim 18 wherein the second insulating material is externally disposed relative to the first insulating material.

22. In combination in a terminal assembly,
a first member,
a second member disposed in spaced relationship to the first member,
a first insulating material disposed between the first and second members in hermetically sealed relationship to the first and second members and having a partially crystalline and partially amorphous composition,
a second insulating material disposed on the first insulating material in external relationship to the first insulating material and in fused relationship to the first insulating material, the second insulating material being hermetically sealed to the first and second members and having a partially crystalline and partially amorphous composition and having a more amorphous composition than the first insulating material, and
a third insulating material having a partially amorphous and partially crystalline composition and disposed on the first insulating material in spaced relationship to the second insulating material and in fused relationship to the first insulating material, the third insulating material being hermetically sealed to the first and second members and having a more crystalline composition than the first insulating material.

23. The combination set forth in claim 22 wherein the second insulating material has non-wetting characteristics relative to the second member and has a domed configuration at its outer end to increase the length of the dielectric leakage path.

24. The combination set forth in claim 23 wherein the third insulating material is provided with a flat configuration at its outer end.

25. The combination set forth in claim 23 wherein each of the first, second and third insulating materials includes the oxides of lead, silicon, boron, zinc and zirconium.

26. The combination set forth in claim 25 wherein the third insulating material also includes an inert filler.

27. The combination set forth in claim 26 wherein the proportions of the oxides of lead, silicon, boron, zinc and zirconium are in substantially the same proportions in the first and third insulating materials.

28. The combination set forth in claim 22 wherein the first, second and third insulating materials are formed from the same chemicals in different proportions to provide the second insulating material with the more amorphous property than the first insulating material and the third insulating material with the more crystalline property than the first insulating material.

29. In combination in a heart pacemaker,
a lid,
a first terminal pin,
a first ferrule disposed on the lid in spaced and enveloping relationship to the first terminal pin,
a second terminal pin,
a second ferrule disposed on the lid in spaced relationship to the first ferrule and in spaced and enveloping relationship to the second terminal pin,
a first insulating material having partially polycrystalline and partially amorphous properties and formed from a particular plurality of chemicals and disposed between the first terminal pin and the first ferrule and hermetically sealed to the first terminal pin and the first ferrule,
a second insulating material having partially polycrystalline and partially amorphous properties and formed from the particular plurality of chemicals and disposed on the first insulating material in fused relationship to the first insulating material and hermetically sealed to the first terminal pin and the first ferrule and having non-wetting characteristics relative to the first ferrule and having a domed configuration and being more amorphous than the first insulating material,
a third insulating material having partially polycrystalline and partially amorphous properties and formed from the particular plurality of chemicals and disposed between the first terminal pin and the first ferrule and hemetically sealed to the first terminal pin and the first ferrule and being more crystalline than each of the first and second insulating materials,
fourth, fifth and sixth insulating materials having compositions, shapes, dispositions and properties relative to the second terminal pin and the second ferrule respectively corresponding to the composition, shapes, dispositions and properties of the first, second and third insulating materials relative to the first terminal pin and the first ferrule, and
an insulating material enveloping the first and second ferrules and the space between the first and second ferrules.

30. The combination set forth in claim 29 wherein the first and fourth insulating materials are respectively more crystalline than the second and fifth insulating materials and less crystalline than the third and sixth insulating materials.

31. The combination set forth in claim 30 wherein the first, second, third, fourth, fifth and sixth insulating materials are formed with the proportions of the chemicals in the second and fifth insulating materials respectively different from the proportions of the chemicals in the first and third insulating materials and in the fourth and sixth insulating materials and the first and fourth insulating materials have a higher melting temperature than the second and fifth insulating materials and a lower melting temperature than the third and sixth insulating materials.

32. The combination set forth in claim 30, including, a filler in the third and sixth insulating materials and the proportions of the particular plurality of chemicals in the first, third, fourth and sixth insulating materials being substantially the same.

* * * * *